United States Patent
He et al.

(10) Patent No.: US 9,260,384 B2
(45) Date of Patent: Feb. 16, 2016

(54) UREA COMPOUNDS AND USE THEREOF FOR INHIBITING APOPTOSIS

(75) Inventors: Kunlun He, Beijing (CN); Song Li, Beijing (CN); Wu Zhong, Beijing (CN); Juan Liu, Beijing (CN); Lili Wang, Beijing (CN); Xin Li, Beijing (CN); Guoliang Hu, Beijing (CN); Long Long, Beijing (CN); Junhai Xiao, Beijing (CN); Zhibing Zheng, Beijing (CN); Wei Li, Beijing (CN); Ruijun Li, Beijing (CN); Chunlei Liu, Beijing (CN); Jie Bai, Beijing (CN)

(73) Assignee: Chinese PLA General Hospital (CN)

( * ) Notice: Subject to any disclaimer, the term of this patent is extended or adjusted under 35 U.S.C. 154(b) by 206 days.

(21) Appl. No.: 13/697,888

(22) PCT Filed: May 14, 2010

(86) PCT No.: PCT/CN2010/000686
§ 371 (c)(1),
(2), (4) Date: Jan. 21, 2013

(87) PCT Pub. No.: WO2011/140680
PCT Pub. Date: Nov. 17, 2011

(65) Prior Publication Data
US 2013/0123300 A1    May 16, 2013

(51) Int. Cl.
*A61K 31/47* (2006.01)
*C07C 275/28* (2006.01)
*C07D 215/40* (2006.01)

(52) U.S. Cl.
CPC .............. *C07C 275/28* (2013.01); *C07D 215/40* (2013.01)

(58) Field of Classification Search
None
See application file for complete search history.

(56) References Cited

U.S. PATENT DOCUMENTS 6,946,474 B2 * 9/2005 Ali et al. ............ 514/313
2002/0028836 A1  3/2002 Altenbach

FOREIGN PATENT DOCUMENTS

| WO | 0222581 A1 | 3/2002 |
| WO | 2007/015632 A1 | 2/2007 |
| WO | 2007101710 A1 | 9/2007 |

OTHER PUBLICATIONS

Williams et al (Foye's Principles of Medicinal Chemistry, 5th Edition, pp. 59-63, 2002).*
Kai Long et al. Structure—activity relationship studies of salubrinal lead to its active biotinylated derivative. Bioorganic & Medicinal Chemistry Letters. 2005 vol. 15, p. 3849-3852.
Extended European Search Report dated Sep. 6, 2013.
Long et al. "Structure-activity relationship studies of salubrinal lead to its active biotinylated derivative", Bioorganic & Medicinal Chemistry Letters, Pergamon, vol. 15, No. 17, 2005, pp. 3849-3852.
Long K et al. "Structure-activity relationship studies of salubrinal lead to its active biotinylated derivative". Bioorganic & Medicinal Chemistry Letters, 2005, pp. 3849-3852.
Gottlieb RA et al. "Reperfusion injury induces apoptosis in rabbit cardiomyocytes". J Clin Invest, 1994, pp. 94, 1621-1628.
Kawano H et al. "Apoptosis in acute and chronic myocarditis". Jpn Heart J., 1994, pp. 35, 745-750.
Kreider BQ et al. "Enrichment of schwann cell cultures from neonatal rat sciatic nerve by differential adhesion". Brain Research, 207 (1981) 433-444.
Jul. 28, 2014—(JP) Office Action—App 2013-509419—Eng Tran.
Nepomniashchikh LM, Semenova LA, Semenov DE, "Ultrastructural Mechanisms of Myocardial Atrophy in White Rats During Starvation," Biull Eksp Biol Med. Apr. 1989;107(4):477-81 (Abstract Only).
Feb. 24, 2011 (PCT) International Search Report—App PCT/CN2010/000686.

* cited by examiner

*Primary Examiner* — Craig Ricci
(74) *Attorney, Agent, or Firm* — Banner & Witcoff, Ltd.

(57) ABSTRACT

A compound of Formula I, or an isomer, pharmaceutically acceptable salt or solvate thereof, is provided. Also, a composition containing a compound of Formula I, or an isomer, pharmaceutically acceptable salt or solvate thereof, and a pharmaceutically acceptable carrier, excipient or diluents, is provided. Further, use of a compound of Formula I, or an isomer, pharmaceutically acceptable salt or solvate thereof for anti-apoptosis is provided, preventing or treating a disease or disorder associated with apoptosis; especially for protecting cardiomyocyte, preventing or treating a disease or disorder associated with cardiomyocyte apoptosis.

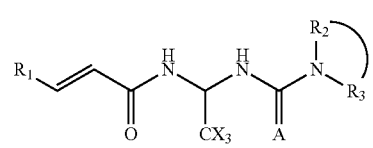

4 Claims, No Drawings

UREA COMPOUNDS AND USE THEREOF FOR INHIBITING APOPTOSIS

The present application is a U.S. National Phase filing of International Application No. PCT/CN2010/000686, filed on May 14, 2010, designating the United States of America. The present application claims priority to and the benefit of the above-identified application, and the above-identified application is incorporated by reference herein in its entirety.

FIELD OF THE INVENTION

The present invention relates to the field of medical chemistry. Specifically, the present invention relates to a urea compound and a pharmaceutical composition thereof. The present invention further relates to use of a urea compound and a pharmaceutical composition thereof for anti-apoptosis, prophylaxis or treatment of a disease or disorder associated with apoptosis, especially for protecting myocardial cells and for prophylaxis or treatment of a disease or disorder associated with apoptosis of myocardial cells.

BACKGROUND OF THE INVENTION

Apoptosis usually refers to programmed cell death of body cells occurring via the regulation of intracellular genes and products thereof during a development process or under the action of some factors. Apoptosis commonly exists in the biosphere under both a physiological state and a pathological state. It plays important roles in embryo development and morphogenesis, stability of normal cells in tissues, defense and immune reaction of body, cell damage caused by diseases or poisoning, ageing, generation and development of tumors, and is one of the hottest spots in biomedical research.

Some researches show that the occurrence of many serious diseases relates to the over apoptosis of cells, for example, the reduction of $CD4^+$ T cells during the development of ADIS; the cell death mediated by cytotoxic T cell during transplant rejection reaction; the apoptosis of myocardial cells and nerve cells of ischemia and reperfusion injury; nervous system degradation diseases (such as Alzheimer disease, Parkinson's disease, etc.); apoptosis caused by exposure to ionizing radiation in many tissues.

Some evidence has indicated that cardiomyocyte apoptosis closely associates with the occurrence, development and prognosis of many heart diseases. It is found in the research about cardiomyocyte apoptosis that the infarct of cardiac muscle is not equivalent to myocardial necrosis, and apoptosis is one of mechanisms of myocardial infarction, and is the main manner of myocardial death of early infarction and myocardial death caused by ischemia/reperfusion, and the apoptosis of cardiomyocytes in large amounts at this time aggravates myocardial damage. In 1989, Nepomniashchikh et al found in the observation of ultrastructure of hunger myocardial atrophy that the synthesis of cardiomyocytes' structural protein decreased, and the cell number decreased but was not accompanied with a proportional decrease of cell nucleus, and thus preliminarily proposed that hunger myocardial atrophy was caused by apoptosis. In 1994, Gottlieb and Kawano et al obtained direct evidence of cardiomyocyte apoptosis by using electron microscope in combination with DNA gel electrophoresis, in which the former disclosed reperfusion injury induced rabbit cardiomyocyte apoptosis, and the latter confirmed that myocarditis patients had concomitant cardiomyocyte apoptosis. Tanaka et al also confirmed the existence of apoptosis of cardiomyocytes in suckling mice. With the progress of methodology and research of apoptosis, pathological functions of cardiomyocyte apoptosis have been found in many heart diseases. Some researches indicate the heart injury in spontaneously hypertensive rat (SHR) is relevant to apoptosis; the conversion from cardiac pachynsis to heart failure in advanced stage is caused by cardiomyocyte apoptosis; acute myocardial infarction also induces apoptosis in early stage of infarction and reperfusion injury, except necrosis; cardiomyocyte apoptosis is also found in transplanted heart and right ventricular maldevelopment myocardial diseases, and anoxia also induces cardiomyocyte apoptosis.

Apoptosis has recoverability in some extents, and the apoptosis in myocardial infarction and ischemia/reperfusion has its own features and regular patterns, so that the features may be used for prevention and reduction of apoptosis and may provide enlightenment for clinical prophylaxis of ischemia/reperfusion injury; during the process of reperfusion, the apoptosis occurring in the contraction band region (around infarction site) is induced by some precipitating factors, so that the inhibition factors of apoptosis such as drugs may be used for preventing apoptosis and treating corresponding diseases caused by apoptosis.

However, there are few kinds and numbers of drugs so far that can be clinically used for anti-apoptosis and protecting cells, and their selectivity and targeting property are not satisfactory, and therefore it is of great significance to continuously develop new, safe and effective drugs for anti-apoptosis and protecting cells, and especially drugs with a novel mechanism of action.

SUMMARY OF THE INVENTION

In order to develop a novel, safe and effective drug for anti-apoptosis and protecting cells, the present inventors find for a long time and by massive experimental research a kind of urea compound that has functions for anti-apoptosis and protecting myocardial cells, and can be useful for prophylaxis or treatment of diseases or disorders associated with cardiomyocyte apoptosis.

Specifically, the first aspect of the present invention relates to a compound of Formula I, or an isomer, a pharmaceutically acceptable salt or a solvate thereof.

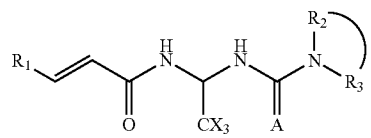

wherein
A represents=O;
X represents F, Cl, Br or I;
R1 represents phenyl, phenyl—C1-C6 alkyl-, wherein said phenyl is unsubstituted or substituted with 1-4 (e.g., 1-2, 1, 2, 3 or 4) substituents independently selected from the group consisting of: halogens, nitro, hydroxyl, amino, cyano, C1-C6 alkyl, C1-C6 alkoxy, and C1-C6 halogenated alkyl, and wherein said alkyl, alkoxy and halogenated alkyl may be optionally substituted with hydroxy, —O—(C1-C4)-alkyl, oxo, amino, —NH—(C1-C4)-alkyl, or —N—[(C1-C6)-alkyl]$_2$, or said alkyl, alkoxy and halogenated alkyl can optionally be intervened by —O—, —S—, —NH—, —COO—, or —CONH—; 5- or 6-membered heterocyclic ring or substituted heterocyclic ring; wherein said heterocyclic ring is unsubstituted or substituted with 1-3 (e.g., 1-2, 1, 2, or 3) substituents independently selected from the group consisting of: halogens, nitro, hydroxyl, amino, cyano, C1-C6 alkyl, C1-C6 alkoxy, and C1-C6 halogenated alkyl, and wherein said alkyl, alkoxy and halogenated alkyl may be optionally substituted with hydroxy, —O—(C1-C4)-alkyl, oxo, amino, —NH—(C1-C4)-alkyl, or —N—[(C1-C6)-alkyl]₂, or said alkyl, alkoxy and halogenated alkyl may be optionally intervened by —O—, —S—, —NH—, —COO—, said heterheterocyclic ring can be nitrogen-nitrogen-containing heterocyclic ring, nitrogen-oxygen-containing heterocyclic ring, nitrogen-sulfur-containing heterocyclic ring;

R2 and R3 represent hydrogen, C1-C6 alkyl, C3-C6 cycloalkyl, substituted C3-C6 cycloalkyl, C1-C6 alkoxy C1-C6 alkyl, aminoC1-C6 alkyl, mono-substituted or di-substituted aminoC1-C6 alkyl, phenyl C1-C06 alkyl, substituted phenyl C1-C6 alkyl, heterocyclic substituent C1-C6 alkyl, substituted heterocyclic substituent C1-C6 alkyl, phenyl, substituted phenyl, C1-C6 heterocyclic substituent or substituted C1-C6 heterocyclic substituent, wherein R2 and R3 may be attached together to form a ring;

Preferably selected is a compound of Formula (I), or an isomer, pharmaceutically acceptable salt and solvate thereof, wherein:

A represents =O;

X represents F, Cl, Br or I;

R1 represents phenyl, phenyl—C1-C6 alkyl-, wherein said phenyl is unsubstituted or substituted with 1-4 (e.g., 1-2, 1, 2, 3 or 4) substituents independently selected from the group consisting of: halogens, nitro, hydroxyl, amino, cyano, C1-C6 alkyl, C1-C6 alkoxo, and C1-C6 halogenated alkyl, and wherein said alkyl, alkoxy and halogenated alkyl may be optionally substituted with hydroxy, —O—(C1-C4)-alkyl, oxo, amino, —NH—(C1-C4)-alkyl, or —N—[(C1-C6)-alkyl]2, or said alkyl, alkoxy and halogenated alkyl can optionally intervened by —O—, —S—, —NH—, —COO—, or —CONH—; thienyl, thiazolyl, wherein said thienyl, thiazolyl is unsubstituted or substituted with 1-3 (e.g., 1-2, 1, 2, or 3) substituents independently selected from the group consisting of: halogens, nitro, hydroxyl, amino, cyano, C1-C6 alkyl, C1-C6 alkoxy, and C1-C6 halogenated alkyl, and wherein said alkyl, alkoxy and halogenated alkyl may be optionally substituted with hydroxy, —O—(C1-C4)-alkyl, oxo, amino, —NH—(C1-C4)-alkyl, or —N—[(C1-C6)-alkyl]2, or said alkyl, alkoxy and halogenated alkyl can optionally be intervened by —O—, —S—, —NH—, —COO—;

R2 and R3 represent hydrogen, C1-C6 alkyl, C1-C6 cycloalkyl, substituted C1-C6 cycloalkyl, C1-C6 alkoxy C1-C6 alkyl, aminoC1-C6 alkyl, mono-substituted or di-substituted aminoC1-C6 alkyl, phenyl C1-C6 alkyl, substituted phenyl C1-C6 alkyl, heterocyclic substituent C1-C6 alkyl, phenyl, substituted phenyl, heterocyclic substituent or substituted heterocyclic substituent, wherein R2 and R3 may be attached together to form a saturated cycloalkyl, nitrogen- or oxygen-containing heterocyclic ring;

In particular, the preferably selected is a compound of Formula (I), or an isomer, pharmaceutically acceptable salt and solvate, wherein:

A represents =O;

X represents Cl;

R1 represents phenyl or 2-thienyl;

R2 and R3 represent hydrogen, methyl, isopropyl, 2-methoxyethyl, 3-isopropoxypropyl, 2-N,N-dimethylethyl, cyclohexyl, cycloheptyl, o-methoxyphenyl, o-fluorophenyl, o-chlorophenyl, p-chlorophenyl, benzyl or 8-quinolyl, wherein R2 and R3 may be attached together to form piperidinyl, morpholinyl or N-methylpiperazinyl.

The compound of Formula (I), or an isomer, pharmaceutically acceptable salt and solvate thereof, is particularly preferably selected from the group consisting of the following compounds:

(1)(2E)-3-phenyl-N-[1-(8-quinolylamino)formylamino-2,2,2-trichloroethyl]-2-acrylamide (2) (2E)-3-phenyl-N-[1-(4-tolylamino)formylamino-2,2,2-trichloroethyl]-2-acrylamide The compound of Formula (I) of the present invention may be prepared by the following method:

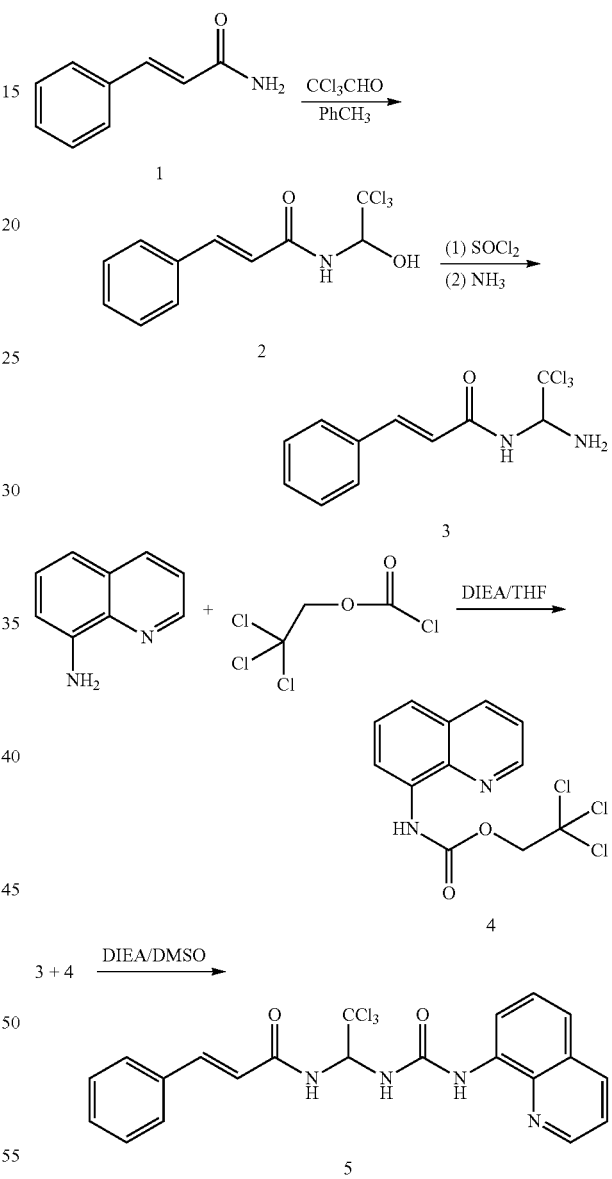

By taking Compound 5 as example, the compound of the present invention is synthesized by using cinnamide as a starting material, reacting with malonic acid in pyridine as solvent under piperidine catalytic condition to generate Compound 2, then reacting with thionyl chloride to prepare an acyl chloride, adding dropwise to a concentrated ammonia water to obtain Compound 3, at the same time, reacting 8-aminoquinoline with trichloroethyl chloroformate to generate Compound 4, reacting 3 with 4 under catalysis of DIEA to prepare Compound 5.

Another aspect of the present invention relates to a pharmaceutical composition, comprising a compound of Formula (I), or an isomer, pharmaceutically acceptable salt or solvate thereof, and a pharmaceutically acceptable carrier, an excipient or a diluent.

The present invention further relates to use of the compound of Formula (I) or an isomer, pharmaceutically acceptable salt or solvate thereof according to the first aspect of the present invention for the manufacture of a medicament for anti-apoptosis, or preventing or treating a disease or disorder associated with apoptosis.

The present invention further relates to a use of the compound of Formula (I) or an isomer, pharmaceutically acceptable salt or solvate thereof according to the first aspect of the present invention for the manufacture of a medicament for protecting cardiomyocytes and preventing or treating a disease or disorder associated with cardiomyocyte apoptosis.

The present invention further relates to a method for anti-apoptosis, or preventing or treating a disease or disorder associated with apoptosis, the method comprising administering to a subject in need thereof a therapeutically effective amount of a compound of Formula (I) or an isomer, pharmaceutically acceptable salt or solvate thereof according to the first aspect of the present invention.

The present invention further relates to a method for protecting cardiomyocyte, or preventing or treating a disease or disorder associated with cardiomyocyte apoptosis, the method comprising administering to a subject in need thereof a therapeutically effective amount of a compound of Formula (I) or an isomer, pharmaceutically acceptable salt or solvate thereof.

The disease or disorder associated with apoptosis according to the present invention comprises: cardiovascular diseases, nerve degenerative diseases, multiple sclerosis, viral infections, etc.

The disease or disorder associated with cardiomyocyte apoptosis according to the present invention includes but is not limited to: (i) hunger myocardial atrophy, (ii) myocarditis, (iii) heart failure, (iv) myocardial damage caused by primary hypertension, (v) myocardial damage caused by early stage of acute myocardial infarction, (vi) myocardial damage caused by acute myocardial infarction reperfusion, (vii) pathological changes of cardiomyocytes caused by heart transplantation, or (viii) displastic mycocardiosis; or cardiomyocyte apoptosis caused by anoxia, or sclerosis in cardiovascular system.

According to the present invention, the term "heterocyclic ring" includes but is not limited to: pyridine, pyrrole, furan, thiophene, pyrazole, imidazole, thiazole, oxazole, isoxazole, indole, benzofuran, benzimidazole, carbazole, pyridazine, pyrimidine, pyrazine, quinoline, isoquinoline, purine, phenothiazine, and phenazine.

Those skilled in the art would appreciate that the compound of Formula I has a chiral center. When a single enantiomer of the compound of Formula I is required, it can be prepared by using reactants present in single enantiomer form in all possible steps, or prepared by performing the reaction in the presence of a reagent or catalyst in single enantiomer form, or prepared by resolution of a mixture of stereoisomers via conventional methods. Some preferable methods comprise resolution using microorganisms, resolution and chiral acid, such as any usable acid, for example mandelic acid, camphor sulfonic acid, tartaric acid, lactic acid, etc. to form a diastereomer salt, or resolution and chiral base such as bracine, cinchona alkaloid or derivatives thereof to form a diastereomer salt. The commonly used methods can be seen in "Enantiomers, Racemates and Resolution" as edited by Jaques et al (Wiley Interscience, 1981).

Those skilled in the art should appreciate that the compound of the present invention can also be used in the form of its pharmaceutically acceptable salt or solvate. The physiologically acceptable salts of the compound of Formula I include conventional salts formed with a pharmaceutically acceptable inorganic acid or organic acid or inorganic base or organic base and acid addition salt of quaternary ammonium. More specific examples of suitable acid salts include salts of hydrochloric acid, hydrobromic acid, sulfuric acid, phosphoric acid, nitric acid, perchloric acid, fumaric acid, acetic acid, propionic acid, succinic acid, hydroxyacetic acid, formic acid, lactic acid, maleic acid, tartaric acid, citric acid, pamoic acid, malonic acid, hydroxymaleic acid, phenylacetic acid, glutamic acid, benzoic acid, salicylic acid, fumaric acid, toluene sulfonic acid, methylsulfonic acid, naphthalene-2-sulfonic acid, benzene sulfonic acid, hydroxynaphthoic acid, hydroiodic acid, malic acid, steroic, tannic acid, etc. As for other acids, such as oxalic acid, although they per se are not pharmaceutically acceptable, they can be used to prepare salts as intermediates to obtain the compound of the present invention and pharmaceutically acceptable salts thereof. More specific suitable alkali salts include salts of sodium, lithium, potassium, magnesium, aluminum, calcium, zinc, N,N'-dibenzylethylenediamine, chloroprocaine, choline, diethanolamine, ethylenediamine, N-methylglucosamine, and procaine. The compounds of the present invention as mentioned thereafter include the compound of Formula I and a pharmaceutically acceptable salt and solvate thereof.

The present invention further comprises a prodrug of the compound of the present invention, and once the prodrug is administered, it is chemically converted via metabolic procedure into an active drug. In general, this kind of prodrug is a functional derivative of the compound of the present invention, which can be readily converted into the needed compound of Formula (I). For example, "Design Of Prodrugs", edited by H Bund Saard, Elsevier, 1985, describes conventional methods of selecting and preparing suitable prodrug derivatives.

The present invention also includes any active metabolites of the compound of the present invention.

Another aspect of the present invention relates to a pharmaceutical composition comprising a racemic or optical isomer of the compound of the present invention, and at least one pharmaceutically acceptable carrier, and being useful in in vivo treatment and having biocompatibility. The pharmaceutical composition can be processed into various forms for different administration routes. The compound of the present invention can also be processed into various pharmaceutically acceptable salts.

The pharmaceutical composition of the present invention comprises an effective amount of the compound of Formula I of the present invention or a pharmaceutically acceptable salt or hydrate thereof and one or more suitable pharmaceutically acceptable carriers. The pharmaceutically acceptable carriers comprise but are not limited to: ion exchangers, alumina, aluminum stearate, lecithin, serum protein such as human albumin, buffering substance such as phosphate, glycerol, sorbic acid, potassium sorbate, mixture of partial glycerides of saturated plant fatty acids, water, salts or electrolytes, such as protamine sulfate, disodium hydrogen phosphate, potassium hydrogen phosphate, sodium chloride, zinc salt, colloid silica, magnesium trisilicate, polyvinylpyrrolidone, cellulose substances, polyethylene glycol, sodium carboxymethylcellulose, polyacrylates, beeswax, and lanolin.

The pharmaceutical composition of the compound of the present invention can be administered by any of the following manners: oral administration, spray inhalation, rectal administration, nasal administration, buccal administration, local administration, parenteral administration, such as subcutaneous, intravenous, intramuscular, intraperitoneal, intrathecal, intraventricular, intrasternal, intracranial injection or perfusion, or administration with aid of an explanted reservoir, preferably oral administration, intraperitoneal or intravenous administration.

For oral administration, the compound of the present invention can be processed in any acceptable forms for oral administration, including but not being limited to tablets, capsules, water solutions or water suspensions. The tablets use a carrier generally comprising lactose and maize starch, additionally comprising a lubricant such as magnesium stearate. The capsules use a diluent generally comprising lactose and dry maize starch. The water suspensions usually use a mixture of an active component and suitable emulsifying agent and suspending agent. If necessary, the above oral dosage forms can further comprise some sweetening agents, flavoring agents or coloring agents.

For local administration, especially in treatment of neurogenic disease of a readily accessible affected surface or organ such as eye, skin or inferior part of intestinal tract by local external application, the compound of the present invention can be processed into different dosage forms for local administration according to different affected surfaces or organs, which are illustrated as follows:

For local administration to eyes, the compound of the present invention can be processed in a dosage form of micronized suspension or solution, in which the used carrier is isotonic sterile saline with a certain pH, wherein a preservative such as chlorobenzylalkanol salt can be added or not be added. For the eye use, the compound can be processed into ointment form, such as Vaseline® ointment.

For local administration to skin, the compound of the present invention can be processed in suitable dosage forms such as ointments, lotions or creams, wherein the active component is suspended or dissolved in one or more carriers. The carriers usable in ointments include but are not limited to: mineral oil, liquid paraffin, white Vaseline®, propylene glycol, polyethylene oxide, polypropylene oxide, emulsified wax and water; the carriers usable in lotions or creams comprise but are not limited to: mineral oil, sorbitan monostearate, Tween® 60, hexadecane ester wax, hexadecylene aromatic alcohol, 2-octyldodecanol, benzyl alcohol and water.

The compound of the present invention can further be administered in dosage form of sterile injections, including water or oil suspensions for sterile injection, or sterile injection solutions. The usable carriers and solvents include water, Ringer's solution and isotonic sodium chloride solution. In addition, sterile nonvolatile oil can also be used as solvent or suspending medium, such as monoglyceride or diglyceride.

It should be further pointed out that the dose and usage method of the compound of the present invention depend on many factors, including age, body weight, gender, natural health status, nutritional status, activity of compound, administration time, metabolic rate, severity of disease and subjective judgment of diagnostic doctor.

BENEFICIAL EFFECTS OF THE INVENTION

The present invention provides a kind of urea compound, and demonstrates it has functions of anti-apoptosis and cell-protection, and thus provides a new method and approach for treatment of diseases or disorders caused by apoptosis, especially for treatment of diseases or disorders caused by cardiomyocyte apoptosis.

Embodiments of the Invention

The embodiments of the present invention are illustrated as follows in combination with examples. However, those skilled in the art would understand that the following examples are merely to illustrate the present invention and should not be deemed as restriction of the present invention. The examples which specific conditions are not given are performed according to conventional conditions or conditions suggested by manufacturers. The reagents or instruments which manufacturers are not given are all conventional products commercially available from markets.

The melting points of compounds were measured by RY-1 melting point instrument, and thermometers were not calibrated. Mass spectra were measured by Micromass ZabSpec high resolution mass spectrometer (resolution: 1000). $^1$H NMR was measured by JNM-ECA-400 superconducting NMR meter, working frequency: $^1$H NMR 400MHz, $^{13}$0 NMR 100MHz.

EXAMPLE 1

(2E)-3-phenyl-N-[1-(8-quinolylamino)formylamino-2,2,2-trichloroethyl]-2-acrylamide

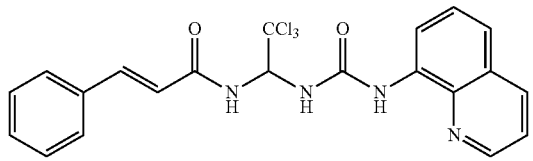

6.50 g of cinnamide and 8.01 g of trichloroacetaldehyde hydrate were dissolved in 300 ml of toluene, refluxed at 110° C. for 8 h, to prepare intermediate (2E)-3-phenyl-N-[1-hydroxy-2,2,2-trichloroethyl]-2-acrylamide. 4.00 g of (2E)-3-phenyl-N-[1-hydroxy-2,2,2-trichloro ethyl]-2-acrylamide was dissolved in 40 ml of anhydrous THF, added dropwise with 4.9 ml of SOCl$_2$ at room temperature, after dropwise adding, heated to 60° C. and refluxed for 3 h. Evaporated to remove solvent, dissolved in 20 ml of anhydrous ethyl ether, added to 20 ml of 0° C. concentrated ammonia water, stirred for 30 min. The layers were separated, and organic layer was evaporated out to obtain intermediate 2.93 g of (2E)-3-phenyl-N-[1-amino-2,2,2-trichloroethyl]-2-acrylamide. 0.58 g of 8-aminoquinoline was dissolved in 8 ml of anhydrous THF, 1 ml of DIEA was added, and cooled to −10° C., 0.56 ml of trichloroethyl chloroformate was added, and reacted for 3 h. Heated to room temperature, 10 ml of ethyl acetate added, 10 ml of water added, shaken or layering, skimmed to obtain organic layer, washed with saline, dried with anhydrous magnesium sulfate, evaporated to remove solvent, then ground with petroleum ether to obtain grey solid 8-(2,2,2-trichloroethformylamino)quinoline 0.69 g. 0.64 g of (2E)-3-phenyl-N-[1-amino-2,2,2-trichloroethyl]-2-acrylamide and 0.69 g of 8-(2,2,2-trichloroethformylamino)quinoline were dissolved in 20 ml of DMSO, 0.4 ml of DIEA added, reacted at 80° C. for 14 h, 20 ml of water and 20 ml of ethyl acetate added, the organic layer was taken and washed with saturated saline, dried with anhydrous magnesium sulfate, evaporated to remove solvent to obtain grey brown powder, eluted with a developing solvent system of dichloromethane : methanol =

100 : 1, to obtain (2E)-3-phenyl-N-[1-(8-quinolylamino)formylamino-2,2,2-trichloroethyl]-2-acrylamide 0.18 g, as white solid.

$^1$H-NMR (400MHz, DMSO-$d_6$) δ6.76-6.78(t,1H); δ6.91-6.95(d,1 H); δ7.40-7.44(m,3H); δ7.53-7.61(m, 6H); δ8.37-8.39(dd,1H); δ8.50-8.58(m,2H); δ8.90-8.91(dd,1H); δ9.06-9.08(d,1 H). MS(TOF) 463.0 (M+).

EXAMPLE 2

(2E)-3-phenyl-N-[1-(4-tolylamino)formylamino-2,2,2-trichloroethyl]-2-acrylamide

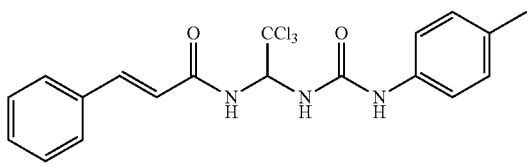

The method of Example 1 was used, in which 8-aminoquinoline was replaced with p-methylaniline, to obtain white solid 0.17 g.

$^1$H-NMR (400MHz,DMSO-$d_6$) δ2.22(s,3H); δ6.62-6.67(t, 1H); δ6.91-6.95(d,1H); δ7.04-7.06(d, 2H); δ7.30-7.33(d, 2H); δ7.40-7.61(m,7H); δ9.18-9.20(d,1 H); δ9.59(s,1 H).MS(TOF)448.0 (M+).

EXAMPLE 3

Experiment on the Activity of the Compound for Protection of Cardiomyocyte

Primary Culture of Cardiomyocyte

The isolation and culture of cardiomyocytes were performed by referring to the differential adhesion method (Kreider, A. Messing, H. Doan, S. U. Kim, R. P. Lisak and D. E. Pleasure, Enrichment of Schwann cell cultures from neonatal rat sciatic nerve by differential adhesion, *Brain Res* 2 (1981), pp. 433-444). Wistar sucking mice newborn within 24 h were used, sterilized at skin of ventrum with iodine tincture and ethanol, subjected to thoracotomy using scissors at subxiphoid median line with a deviation to left, heart was taken out after slant thoracotomy and placed in PBS precooled with ice; the heart was softly blown and beaten with 0.01M PBS to remove blood cells and other tissues, then cut into pieces with 0.5 mm$^3$ size, washed with 0.01 M PBS repeatedly for 2-3 times; the pieces were placed in conical flask, added with 4 ml of 0.125% pancretin, 1 ml of 0.1% collagenase II (final concentrations separately being 0.1% and 0.02%), shaken in 37° C. water bath for 10 min, the supernatant was discarded; then 4 ml of 0.125% pancretin and 1 ml of 0.1% collagenase II again, shaken in 37° C. water bath for digestion for 10 min, the supernatant was sucked and transferred to a centrifuge tube, and the supernatant was added with DMEM containing 10% FBS to terminate digestion; the step of shaking and digestion in water bath was repeated for 3-4 times, until the tissue pieces were completely digested; the collected cell suspension was centrifuged under 1000 rpm for 10 min, the supernatant was removed, then a culture medium was added for resuspension; the resuspended cells were inoculated in a cell culture flask, placed in $CO_2$ incubator at 37° C. for incubation for 1.5 h, then the culture medium was sucked out, countered under microscope, then DMEM culture medium containing 10% FBS was used to adjust cell density, inoculated in an amount of $1\times10^4$ to a 96-well plate, placed in 5% $CO_2$ incubator at 37° C. for 24 h, then half medium was replaced, a culture medium containing 0.1% Brdu was supplementally added; then the medium was replaced once per 48 h, and primary cardiomyocytes were obtained after 4 days of cultivation.

Measurement of Cell Inhibition Rate (MTT)

The isolated primary culture of cardiomyocytes was inoculated in an amount of $10^4$ cells per well to a 96-well plate, and the volume of each well was 100 ul (marginal wells were filled with sterile PBS). After being cultivated in 5% $CO_2$ and 37° C. incubator for 4d, they were added with the compound of Formula I in different concentrations (0.3 μM, 1 μM, 3 μM, 10 μM, 30 μM, 100 μM), 3 double-wells were set for each concentration, at the same time, zero setting wells (culture medium, MTT, DMSO), and control wells (culture medium, DMSO) were also set. After continuous inoculation for 48 h, each well was filled with 20 ul of MTT solution (5 mg/ml, formulated with PBS (pH=7.4), i.e., 0.5% MTT), and the cultivation was continued for 4 h. After the end of cultivation, culture medium in wells was carefully sucked out. Each well was filled with 150 ul of DMSO, shaken at a low speed in a shaking table for 10 min, so that the crystal was sufficiently dissolved. The optical density (OD) value of each well was measured at wavelength of 550 nm by enzyme-linked immunoassay instrument, and each well was repeatedly measured for 5 times and the results were recorded.

TABLE 1

Effects of the compound at different concentrations on survival rate of the cardiomyocytes as assayed by the MTT method

| Group | inhibition rate (%) of cardiomyocytes |
|---|---|
| Control group | 100 |
| Compound of Example 1 | |
| 30 μM group | 9.57 ± 1.62 |
| 300 μM group | 7.78 ± 3.42 |

Notation: cell survival rate = 1 − cell inhibition rate

Test results: the compound of Example 1 at a concentration within 300 μM has no effect on survival rate of normal cardiomyocytes.

Assay of the activity for protection of cardiomyocytes: activity for protecting cardiomyocytes apoptosis induced by TG Cardiomyocytes were subjected to the primary culture for 4 days according to the above method, and then thapsigargin (TG) was added to induce apoptosis. The compound of the present invention was added for pretreatment 30 min before inducing apoptosis. The cells were randomly divided into 5 groups: (1) solvent control group (DMSO); (2) TG intervening group (0.4 uM); (3) TG (0.4 uM)+compound intervening group (0.3 uM); (4) TG (0.4 uM)+compound intervening group (1 uM); (5) TG (0.4 uM)+compound intervening group (3 uM). TG was formulated with DMSO, the mother liquid was of 4 mM; and the compound of the present invention was formulated with DMSO, and the mother liquid was of 150 mM. The cell survival rate was measured according to the above MTT method, so as to test the protection effects of the compound of the present invention on the TG-induced cardiomyocytes apoptosis, and the results are shown in Table 2.

TABLE 2

Effects of the compound at different concentrations on TG-induced cardiomyocytes apoptosis as assayed by the MTT method

| Group | Cardiomyocyte survival rate (%) |
| --- | --- |
| Control group | 100 |
| TG intervening group | 59 ± 1.1 |
| Compound of Example 5 | |
| 0.3 μM group | 79.3 ± 4.6 |
| 1 μM group | 83.8 ± 8.3 |
| 3 μM group | 84.2 ± 1.1 |

The experimental results: in comparison with the group with TG alone added, the survival rate of the cardiomyocytes was significantly increased when TG and the compound of the Example were added together, indicating that the compound of the Example as indicated in Table 2 can significantly improve TG-induced apoptosis and has a protection effect on the cardiomyocytes.

Although the embodiments for carrying out the invention have been described in details, those skilled in the art would understand that according to the disclosed teachings, these details could be subjected to various modifications and replacements, and all of these alternatives are covered by the protection scope of the present invention. The protection scope of the present invention is determined by the attached claims and any equivalents thereof.

What is claimed is:

1. A compound or an isomer, pharmaceutically acceptable salt or solvate thereof, wherein the compound has one of the following structures:
   (1) (2E)-3-phenyl-N-[1-(8-quinolylamino)formylamino-2,2,2-trichloroethyl]-2-acrylamide; and
   (2) (2E)-3-phenyl-N-[1-(4-tolylamino)formylamino - 2,2,2-trichloroethyl]-2-acrylamide.

2. A pharmaceutical composition comprising at least one compound or an isomer, pharmaceutically acceptable salt or solvate thereof according to claim 1, and a pharmaceutically acceptable carrier, excipient or diluent.

3. A pharmaceutical composition according to claim 2, wherein the pharmaceutically acceptable carrier is selected from the group consisting of ion exchangers, alumina, aluminum stearate, lecithin, serum protein, phosphate, potassium sorbate, a mixture of partial glycerides of saturated plant fatty acids, protamine sulfate, disodium hydrogen phosphate, potassium hydrogen phosphate, sodium chloride, zinc salt, colloid silica, magnesium trisilicate, polyacrylates, beeswax, isotonic sterile saline, lanolin, mineral oil, liquid paraffin, propylene glycol, polyethylene oxide, polypropylene oxide, emulsified wax, sorbitan monostearate, hexadecane ester wax, hexadecylene aromatic alcohol, 2-octyldodecanol, benzyl alcohol, Ringer's solution, isotonic sodium chloride solution, a sterile nonvolatile oil and combinations thereof.

4. A compound or an isomer, pharmaceutically acceptable salt or solvate thereof according to claim 1, wherein the compound reduces cardiomyocyte apoptosis.

* * * * *